United States Patent
Lo et al.

(10) Patent No.: US 8,500,278 B2
(45) Date of Patent: Aug. 6, 2013

(54) APPARATUS AND METHOD FOR OBJECTIVE PERIMETRY VISUAL FIELD TEST

(75) Inventors: Patrick Lo, Vancouver (CA); Liang Chen, Prince George (CA); Chi Ho To, Kowloon (CN)

(73) Assignees: Liang Chen, Prince George (CA); Patrick Lo, Vancouver (CA)

( * ) Notice: Subject to any disclaimer, the term of this patent is extended or adjusted under 35 U.S.C. 154(b) by 161 days.

(21) Appl. No.: 12/530,282

(22) PCT Filed: Mar. 7, 2008

(86) PCT No.: PCT/CA2008/000472
§ 371 (c)(1),
(2), (4) Date: Jan. 26, 2010

(87) PCT Pub. No.: WO2008/106802
PCT Pub. Date: Sep. 12, 2008

(65) Prior Publication Data
US 2010/0149488 A1 Jun. 17, 2010

Related U.S. Application Data

(60) Provisional application No. 60/893,800, filed on Mar. 8, 2007.

(51) Int. Cl.
*A61B 3/14* (2006.01)
*A61B 3/10* (2006.01)
(52) U.S. Cl.
USPC .............................. 351/206; 351/209; 351/211

(58) Field of Classification Search
USPC .......................................... 351/206, 209, 211
See application file for complete search history.

(56) References Cited

U.S. PATENT DOCUMENTS

| | | |
|---|---|---|
| 3,718,386 A | 2/1973 | Lynn et al. |
| 3,883,235 A | 5/1975 | Lynn et al. |
| 4,059,348 A | 11/1977 | Jernigan |
| 4,392,725 A | 7/1983 | Sheingorn |
| 4,813,779 A | 3/1989 | Schneider et al. |
| 5,220,361 A | 6/1993 | Lehmer et al. |
| 5,319,398 A | 6/1994 | Weijland |
| 5,459,536 A | 10/1995 | Shalon et al. |
| 5,491,757 A | 2/1996 | Lehmer et al. |
| 5,880,812 A | 3/1999 | Solomon |
| 5,920,375 A | 7/1999 | Fahle et al. |
| 5,953,102 A | 9/1999 | Berry |

(Continued)

FOREIGN PATENT DOCUMENTS

| | | |
|---|---|---|
| GB | 2096791 A | 10/1982 |
| WO | 9840781 | 9/1998 |

OTHER PUBLICATIONS

International Search Report and Written Opinion, Jun. 3, 2008.

*Primary Examiner* — Mahidere Sahle
(74) *Attorney, Agent, or Firm* — Oyen Wiggs Green & Mutala LLP

(57) ABSTRACT

Apparatus for testing a subject's visual field includes a data processor, which can be provided by a general purpose computer, coupled to a pupil tracking system. The data processor is programmed to cause targets to be displayed at different locations on a display screen and to determine from the pupil tracking system whether the subject's pupil has moved in response to display of each target. In some embodiments, the pupil tracking system comprises an infrared camera.

23 Claims, 6 Drawing Sheets

U.S. PATENT DOCUMENTS

| | | |
|---|---|---|
| 6,290,357 B1 | 9/2001 | Massengill et al. |
| 6,367,932 B1 | 4/2002 | Donaldson |
| 6,494,578 B1 | 12/2002 | Plummer et al. |
| 6,527,391 B1 | 3/2003 | Heijl et al. |
| 6,736,511 B2 | 5/2004 | Plummer et al. |
| 6,783,240 B2 | 8/2004 | Matsumoto |
| 7,682,026 B2 * | 3/2010 | Huffman et al. ............... 351/210 |
| 2004/0174496 A1 * | 9/2004 | Ji et al. .......................... 351/209 |
| 2006/0110008 A1 | 5/2006 | Vertegaal et al. |
| 2006/0114414 A1 | 6/2006 | McGrath et al. |
| 2011/0157550 A1 * | 6/2011 | Chen et al. .................... 351/206 |

* cited by examiner

GRID REPRESENTING SUBJECT'S RETINA

GRID REPRESENTING DISPLAY SCREEN

APPARATUS AND METHOD FOR OBJECTIVE PERIMETRY VISUAL FIELD TEST

REFERENCE TO RELATED APPLICATION

This application claims priority from U.S. patent application No. 60/893,800 filed 8 Mar. 2007. For purposes of the United States, this application claims the benefit under 35 U.S.C. §119 of U.S. patent application No. 60/893,800 filed 8 Mar. 2007 which is hereby incorporated herein by reference.

TECHNICAL FIELD

This invention relates to apparatus and methods for visual field testing.

BACKGROUND

"Visual field" means the spatial array of visual sensations available for observation by a subject. "Field of view" means the physical objects and light sources in the external world that impinge the subject's retina. In other words, field of view is everything that (at a given time) causes light to fall onto the retina. The field of view is processed by the visual system, which computes the visual field as the output. In optometry and ophthalmology a visual field test is used to study a subject's visual field.

There are many pathological causes of visual deterioration. The pathology can involve the eye itself, the optic nerve, or the neuro-visual pathways in the brain. Knowledge of the visual field together with other ophthalmologic characteristics can help to localize the probable site of the pathology. Certain diseases can cause local scotoma or more extensive losses of vision. Visual field testing may be applied to determine whether the visual field of a subject is affected by disease. In addition to various disorders of the eye a visual field test can be used to help diagnose neurological disorders such as pituitary adenomas (very common brain tumors), meningiomas, cavernous angioma, anterior ischemic optic neuropathy, aneurysm and strokes.

Visual field testing may be performed by a technician directly, by a technician with the assistance of a machine, or by an automated machine. Names applied to visual field testing include perimetry, tangent screen exam, automated perimetry exam, Goldmann visual field exam, or Humphrey field exam. "Perimetry" is the systematic measurement of differential light sensitivity in the visual field by the detection of the presence of test targets on a background.

Techniques for visual field testing include:
Confrontation visual field exam—An examiner asks the subject to cover one eye and stare at the examiner. The examiner then moves a hand out of the subject's visual field and then brings it back in. The subject signals the examiner when the hand comes back into view.
Tangent screen exam or Goldmann field exam—The subject is asked to sit in front of a screen with a target on the center. The eye that is not being tested is covered. While the subject stares at the target the examiner moves an object toward the subject's visual field. The subject signals the examiner when the object comes into view. This exam allows the subject's visual field to be mapped.
Automated perimetry exam—The subject sits in front of a concave dome with a target in the center. The eye that is not being tested is covered. A button is given to the subject to be used during the exam. The subject is set in front of the dome and asked to focus on the target. A computer then causes lights to shine on the inside of the dome and the subject clicks the button whenever a light is seen. The computer then automatically maps and calculates the subject's visual field.
Human visual perception is dynamic. It responds well to moving targets. Current instruments for visual field testing typically utilize either a static or a kinetic (moving) dot in detecting scotomas (blind spots).

Current instruments for visual field testing generally have a degree of subjectivity. They require that the subject's eye remain fixed on a non-moving feature, normally in the center of a screen, while many targets, usually of equal size, are presented in different areas of the subject's visual field. The subject is required to press a button or otherwise deliberately indicate when a target is detected. The required fixation tends to quickly induce fatigue. In addition, the tests tend to be lengthy which further increases fatigue. The requirement for fixation, which is difficult to maintain coupled with the induced fatigue together with the need for a subjective response tends to limit the accuracy. Generally the display of current instruments is curved so that a target is presented at approximately the same distance from the eye being checked anywhere on the screen.

Technology relating to eye testing is disclosed in the following United States patents:
U.S. Pat. No. 3,718,386
U.S. Pat. No. 3,883,235
U.S. Pat. No. 4,059,348
U.S. Pat. No. 4,392,725
U.S. Pat. No. 5,220,361
U.S. Pat. No. 5,319,398
U.S. Pat. No. 5,459,536
U.S. Pat. No. 5,491,757
U.S. Pat. No. 5,880,812
U.S. Pat. No. 5,953,102
U.S. Pat. No. 6,494,578
U.S. Pat. No. 6,527,391
U.S. Pat. No. 6,736,511
U.S. Pat. No. 6,783,240

There are a variety of devices which work on a variety of principles and purport to be able to track the direction of vision of an eye. Recent studies on active illumination-based approaches show that a multiple infrared (IR) source-synchronized, or active IR, camera is able to robustly locate human pupils under different illumination conditions, even for people wearing eye glasses, from considerable distances.

SUMMARY

The invention has a range of aspects. Some of the aspects provide methods for visual field testing. Some of the aspects provide apparatus for visual field testing. Some of the aspects provide program products bearing computer-readable instructions that can be executed by an appropriate data processor to cause the data processor to be useful in visual field testing.

One aspect of the invention provides a method for performing objective perimetry visual field testing of a subject's eyes. The method comprises providing an eye tracking device in data communication with a personal computer or other data processing device having one or more display screens, displaying targets in sequence on one of the one or more display screens while the subject views the display screen with an eye under test; and recording whether the eye under test moves in response to the presentation of a target.

Another aspect of the invention provides apparatus for visual field testing that includes an eye tracking device in data communication with a personal computer or other data processing device connected to display targets on a display screen. In embodiments the display screen is essentially flat. In some embodiments, the display screen comprises a computer monitor connected to the data processing device. The data processing device is configured to perform visual field testing.

In some embodiments, the eye tracking device includes an active IR camera. Data from the IR camera is used by the computer to determine the direction of gaze of an eye.

In an aspect of the invention, the object on the screen of a computer monitor or similar display device is first presented as a single small point, then dynamically enlarged until a response occurs. The direction and speed of enlargement is controlled. When the initial target is within the confines of a real scotoma, the enlarging target will eventually cross the scotoma's boundary and elicit a response. For those cases where the scotoma is substantially large, such as hemianopsia (half-field loss as in stroke victims), this technique could save a great deal of time needed for the testing. Refining tests may be conducted to determine the exact intact areas of visual fields.

In addition to the exemplary aspects and embodiments described above, further aspects and embodiments will become apparent by reference to the drawings and by study of the following detailed description.

BRIEF DESCRIPTION OF DRAWINGS

Exemplary embodiments are illustrated in referenced figures of the drawings. The embodiments and figures disclosed herein are illustrative and not restrictive.

DESCRIPTION

Figure 1:
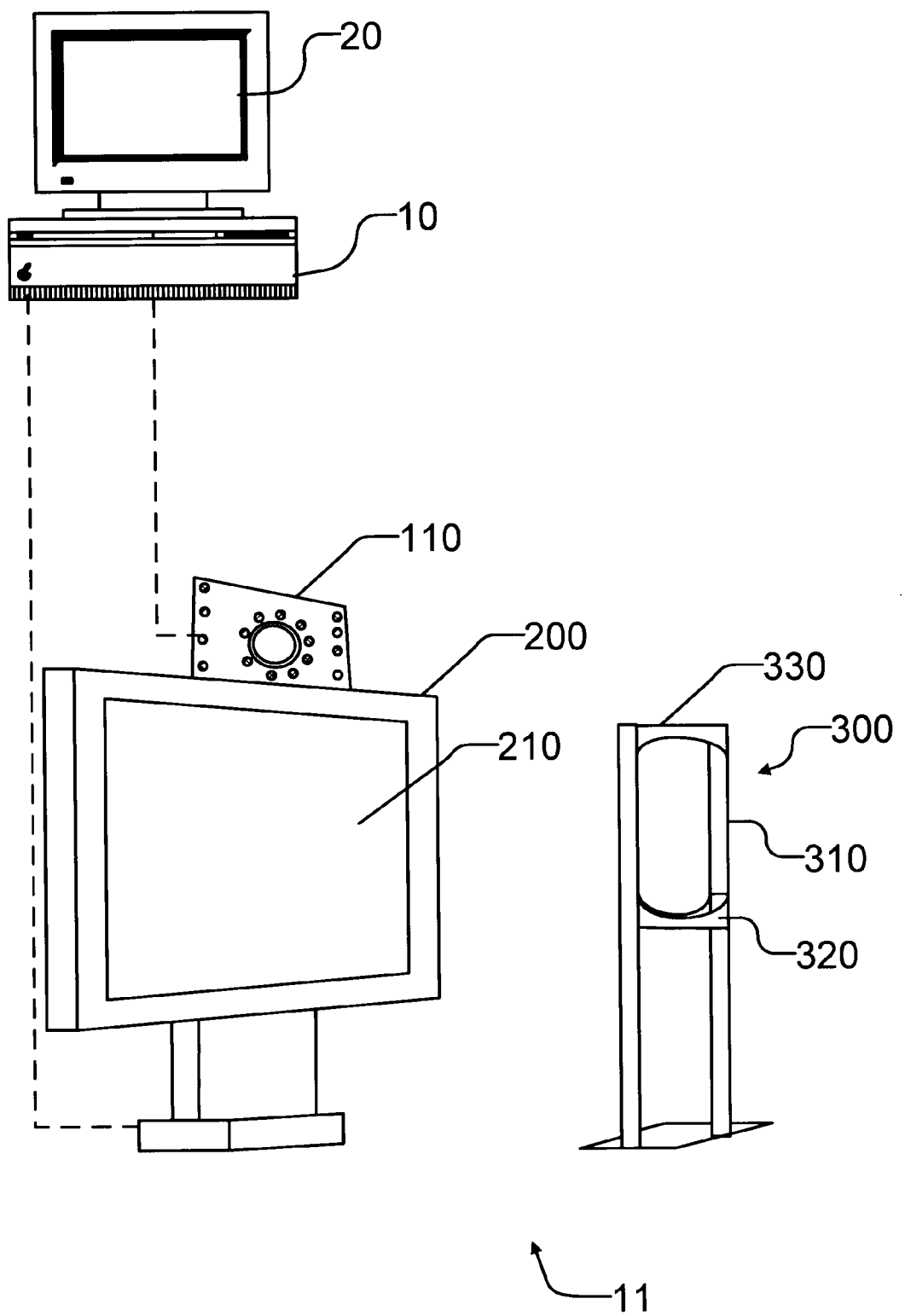
FIG. 1 is a perspective view of apparatus according to an example embodiment.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

With reference to FIGS. 1 to 8, apparatus 11 according to an example embodiment comprises a personal computer 10. Computer 10 may include components and peripherals normally associated with a personal computer. Computer 10 is connected to and controls a primary display 200 and a second optional monitor 20. It is not mandatory that computer 10 be a personal computer. Computer 10 may comprise any suitable data processing device such as an embedded processor, microprocessor, application server, networked computer, or the like.

In the illustrated embodiment, display 200 comprises a computer monitor. The monitor may have a flat screen. The monitor may, for example, comprise an LCD display, plasma display CRT display, or the like.

A gaze detection system 13 is provided to determine a direction of gaze of a subject. Gaze detection system may comprise a suitable pupil tracking system. In the illustrated embodiment, gaze detection system 13 comprises a camera 110 that images a subject's eye and determines a direction of the subject's gaze based on image data from camera 110. In some embodiments, image data from camera 110 is passed to computer 10 and processed on computer 10 to track the direction of the subject's gaze. In the alternative, gaze detection system 13 may have a dedicated system for processing image data from camera 110.

Figure 2:
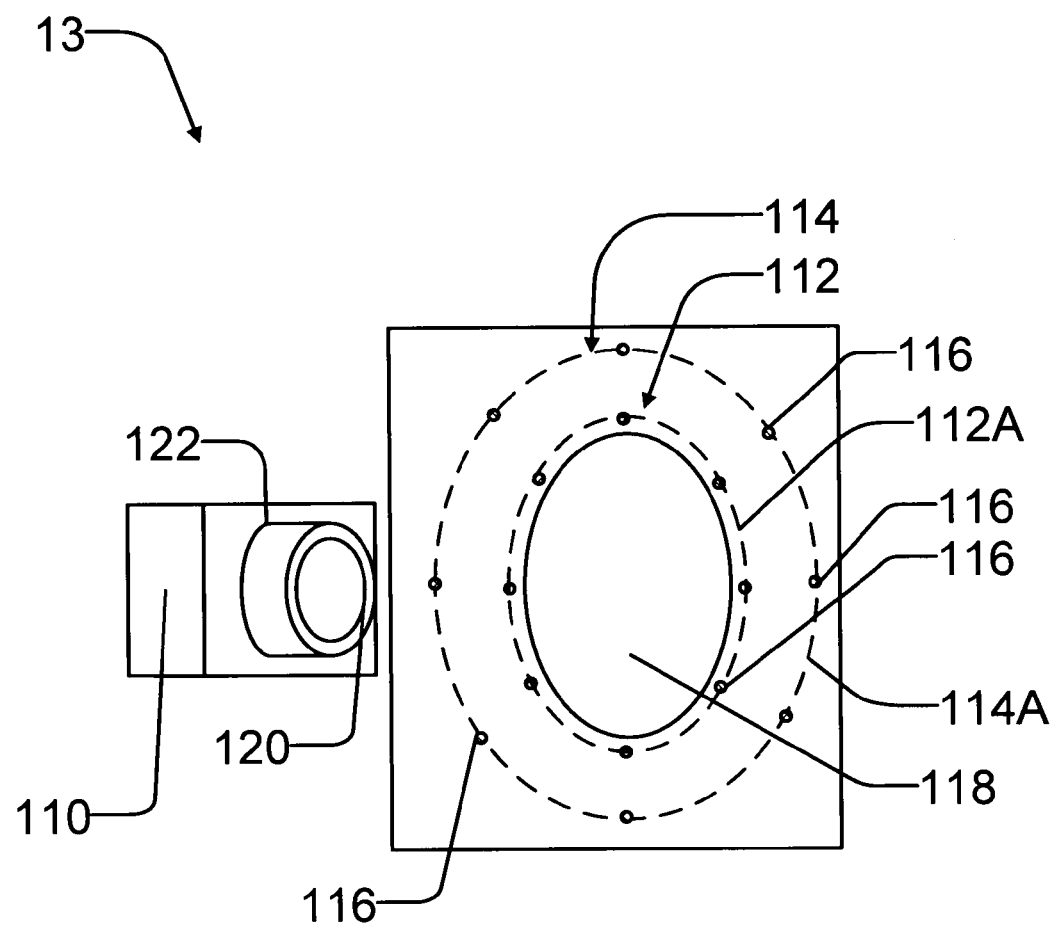
FIG. 2 illustrates an IR camera of a type that may be used in the embodiment of FIG. 1.

In some embodiments, camera 110 comprises an infrared (IR) camera as illustrated, for example, in FIG. 2. Movements of the subject's pupil are detected with the IR camera.

In the illustrated embodiment, apparatus 11 comprises a head rest 300. Head rest 300 serves to keep a subject's head relatively motion free in relation to active IR camera 110 at a desired position relative to primary display 200. The subject's eye being tested may be at any suitable distance from the screen 210 or primary display 200. For example, the subject's eye could be 50 cm or so from screen 210. Where screen 210 is larger then the distance from the subject's eye to screen 210 may be larger and when screen 210 is smaller then the subject's eye should be closer to screen 210. Screen 210 may have any suitable size greater than about 50 cm (measured diagonally).

Headrest 300 comprises a frame 310, a chinrest 320, and a forehead rest 330. Headrest 300 is optional. With appropriate gaze detection means, it is possible to detect the direction of the subject's gaze, and hence to determine the point of gaze on primary display 200, without a headrest. The use of a high-backed chair (not shown) can also help to reduce a subject's head movement.

Apparatus 11 may be applied to identify blind spots or blind areas by displaying targets on display 200 and tracking any resulting eye movements of the subject. In one aspect of the invention, a subject is instructed to direct the eye under test towards any target appearing on primary display 200. Under control of computer 10, targets are presented at different points on primary display 200. Data from active IR camera 110 is used by computer 10 to determine the direction of gaze of the eye being tested. Knowing the direction of the gaze and the position of the eye relative to primary display 200, the point of gaze on primary display 200 is calculated as further described below.

When vision is intact, the eye will naturally tend to move to a new target presented on display 200. This reinforces the command to allow the eye to move to a new target. When a target appears on primary display 200 in a region of the subject's visual field where vision is severely impaired, the new target is not detected and the eye does not move to the position of the new object. The movement or lack of movement of the eye in response to the presentation of the new target is recorded by the computer 10.

In the embodiment illustrated in FIG. 1, information relevant to operating apparatus 11 may be displayed on second monitor 20. A second monitor is optional. It would be possible to configure apparatus 11 so that information relevant to the operation of apparatus 11 is displayed, at appropriate times, on primary display 200. This latter option may be desirable in the interests of economy, or portability or for other reasons.

Personal computer 10 could be, for example, a laptop computer in which case second monitor 20 might be incorporated into the computer along with all the normal components and peripherals such as keyboard, mouse, central processing unit, mass storage device(s) etc.

As shown in FIG. 2, pupil detection and tracking system 13 comprises two illuminators 112 and 114. For convenience illuminators 112 and 114 may comprise near infrared sources which emit light at a wavelength or wavelengths that are invisible or almost invisible to the human eye. For example, illuminators 112 and 114 may emit light at a wavelength of about 875 nm. Camera 110 is sensitive at wavelengths emitted by illuminators 112 and 114.

Illuminator 112 is arranged to provide a bright pupil image while illuminator 114 is arranged to provide a dark pupil image. This is achieved in the illustrated embodiment by placing light sources of illuminator 112 close to an optical axis 120 of lens 122 of camera 110. Light sources of illuminator 114 are placed farther from optical axis 120. In the illustrated example embodiment of FIG. 2, illuminators 112, 114 each comprise eight IR emitting diodes (LEDs) 116. The LEDs are distributed in two concentric rings 112A, 114A. The center 118 of the rings coincides with the camera optical axis 120.

In an example embodiment, both rings are in the same plane. Inner ring 112 is sufficiently close to the camera optical axis 120 to generate a bright pupil image. The diameter of outer ring 114A is sufficiently large (the LEDs 116 and are far from the camera's optical axis 120) to generate a dark pupil image) and is sufficiently bright to generate approximately the same illumination as the inner ring 112. In the example embodiment, inner ring 112A has a diameter approximately the same as the diameter of lens 122 (15 mm), and outer ring 114A has a diameter of about: 90 mm. These values are obtained empirically, and are dependent on the specifics of the camera. In another embodiment, outer ring 114A is replaced by two parallel lines 114B of LEDs 116 spaced approximately 75 mm from the camera lens 122 as shown in FIG. 1. First and second illuminators 112 and 114 may comprise other arrangements of light sources.

Gaze tracking system controls illuminators 112 and 114 so that camera 110 obtains some images of the subject's eye illuminated by illuminator 112 and other images of the subject's eye illuminated by illuminator 114. For example, illuminators 112 and 114 may be switched on and off in a way that is synchronized with the operation of camera 110 such that even and odd frames of the camera are illuminated by illuminators 112 and 114 respectively. For example, an even frame is grabbed when LEDs of inner ring 112A are on and an odd frame is grabbed when the LEDs of outer ring 114 are on.

A variety of techniques have been published and will be known to one skilled in the art to locate pupil position. Any suitable technique for locating pupil position or for otherwise determining the direction of the subject's gaze may be applied in embodiments of the invention. A basic embodiment of an algorithm that may be applied for locating the subject's pupil in images from camera 110 is as follows. Let:

$F_e$ be data for an even frame and $F_o$ be data for an odd frame. Both frames are, or are converted to, grayscale.

$E_{i,j}$ be the pixel in the $i^{th}$ column and $j^{th}$ row of the odd frame and $O_{i,j}$ be the pixel in the same location in the even frame.

$F_d$ be the difference between the two frames.

$F_d$ is computed as:

$$D_{ij} = ABS(E_{ij} - O_{ij}) \quad (1)$$

where $D_{i,j}$ is the pixel in the $i^{th}$ column and $j^{th}$ row of $F_d$.

Compute the sums of the values of the pixels for every column i in $F_d$. Let colMax be the maximum of these sums. Find the sums of the values of the pixels for every row j in $F_d$. Let rowMax be the maximum of these sums. The centre of the pupil is located at (rowMax, colMax). Other suitable algorithms may also be used.

There are three distinct coordinate spaces relevant to pupil tracking and eye testing: camera coordinates, screen coordinates and eye coordinates. Camera coordinates identify the location in images obtained by camera 110 at which the subject's pupil is located. The algorithm described above may be applied, for example, to determine the camera coordinates for the subject's pupil.

Screen coordinates identify the location on primary display 200 that the subject's eye is looking at. Screen coordinates can be determined from the location of the pupil specified in camera coordinates of camera 110 and a transformation function.

Figure 5:
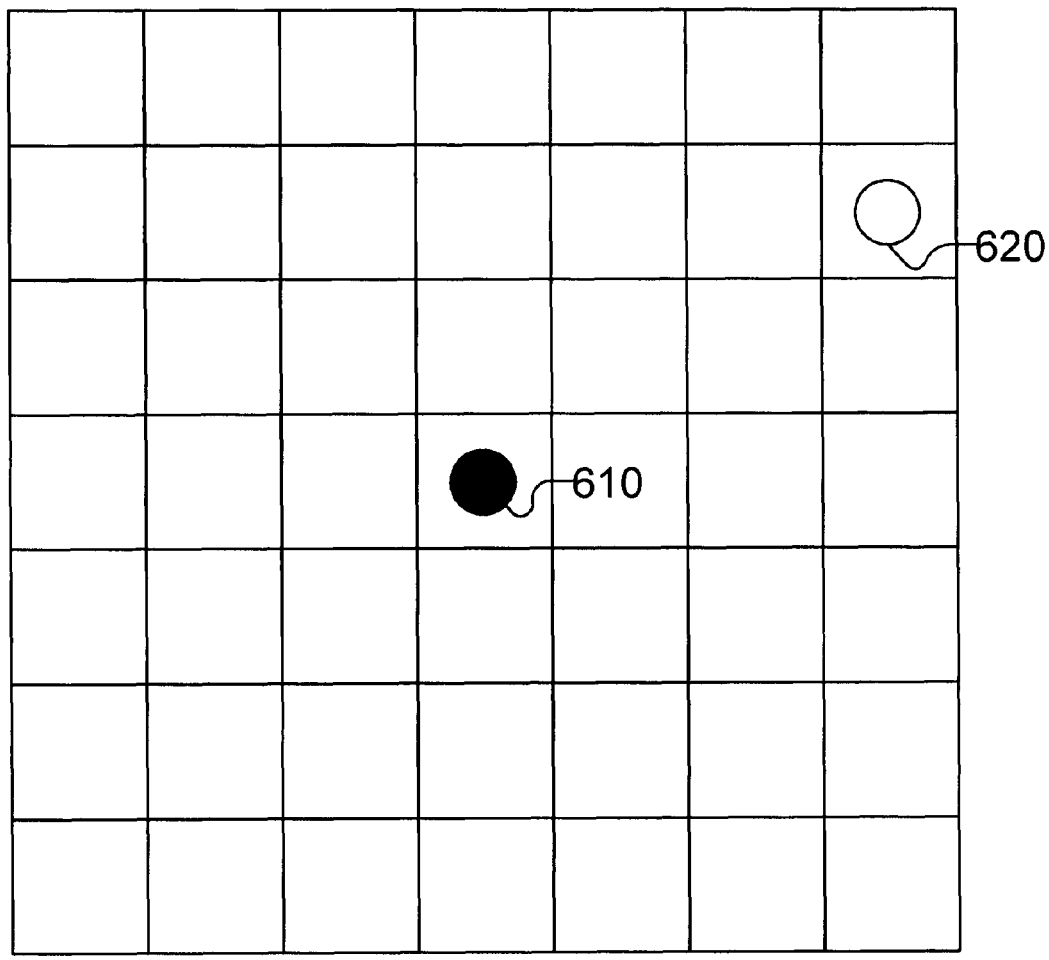
FIG. 5 is shows a grid representing the retina.
Figure 6:
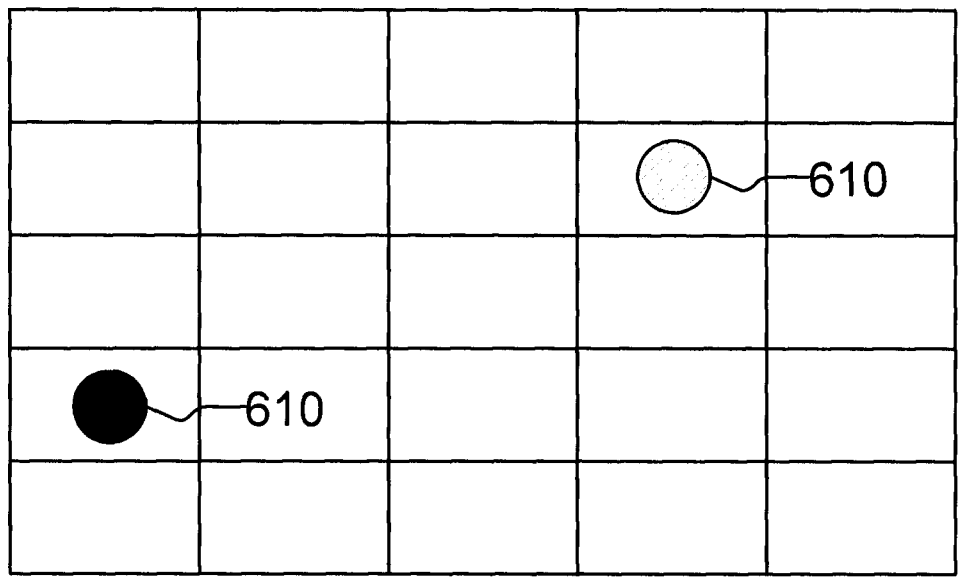
FIG. 6 shows a grid representing the primary monitor (screen grid).

Eye coordinates identify the region of the subject's eye, as shown in FIG. 5, that sees the current target 620. Eye coordinates can be determined from the relative screen coordinates of the location at which a subject is currently gazing (which is typically the position of a previous target 610 that the subject has seen) and the current target 620, as shown in FIG. 6.

Assuming that the subject is located directly in front of camera 110 and that primary display 200 is rectangular, a trapezoid t in camera coordinates corresponds to the area of primary display 200 in screen coordinates. A transformation function relates camera coordinates and screen coordinates may be established by determining camera coordinates corresponding to at least three points having known screen coordinates that are not collinear. In an example embodiment, the location of the pupil in camera coordinates is established at each of the four corners of primary display 200 and a mathematical function that maps between the resulting trapezoid in camera coordinates and a rectangle that describes screen coordinates is generated.

Figure 3:
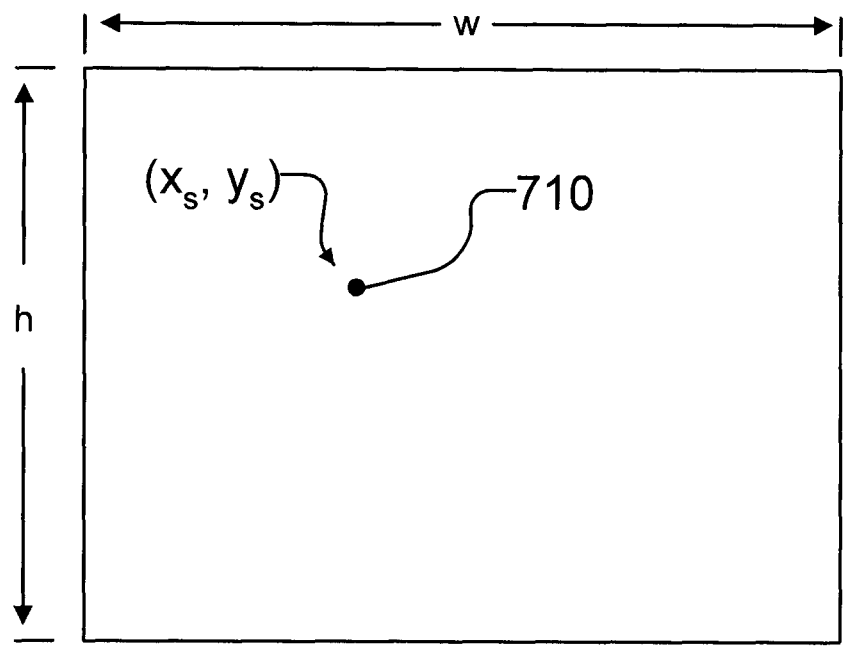
FIG. 3 shows the screen of a primary monitor in the embodiment of FIG. 1.

In FIG. 3, which shows screen 210 of primary display 200, w and h are the width and height, respectively, of screen 210 in pixels. Let $(x_s, y_s)$ be the point 710 on primary display 200 at which the pupil is currently looking.

Figure 4:
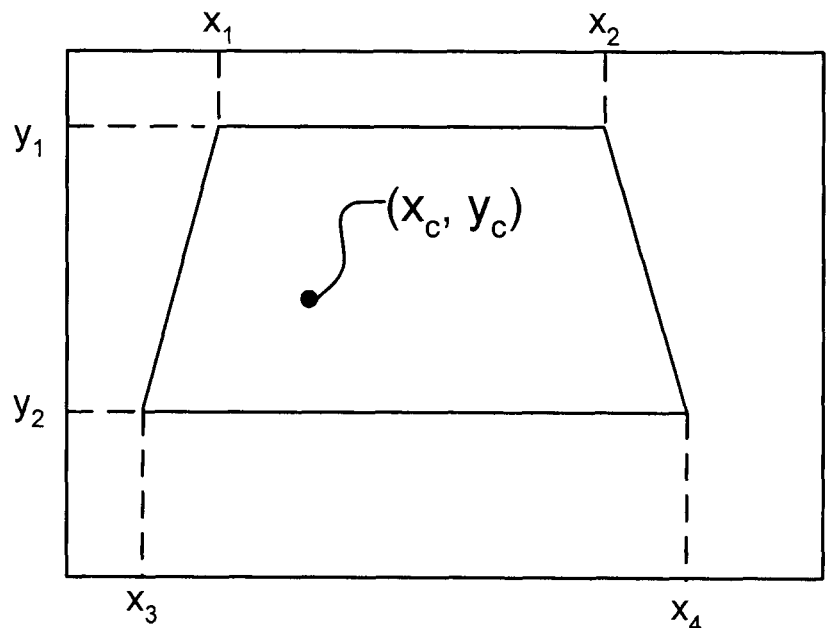
FIG. 4 illustrates a trapezoid used in calculating the point of gaze on the primary monitor.

FIG. 4 details trapezoid t, with top and bottom at $y_1, y_2$ respectively, and with x-coordinates at $x_1, x_2, x_3, x_4$ for the top left, top right, bottom left and bottom right x-coordinates respectively. $(x_c, y_c)$ is the location of the pupil in camera coordinates and $(x_s, y_s)$ is the location 710 on the primary display 200 at which the eye is looking (point of gaze 710 on display 200).

To find a mapping between $(x_c, y_c)$ and $(x_s, y_s)$, let $d(x,y)$ be the distance from $(x,y)$ to the left side of the trapezoid and $w(y)$ be the width of the trapezoid at y. It can be shown that:

$$d(x, y) = x - x_1 + \frac{y - y_1}{y_2 - y_1}(x_1 - x_3) \quad (2)$$

$$w(y) = x_2 - x_1 + \frac{y - y_1}{y_2 - y_1}(x_1 + x_4 - (x_3 + x_2)) \quad (3)$$

$$x_s = \frac{d(x_c, y_c)}{w(y_c)} w \quad (4)$$

$$y_s = (y_c - y_1)\frac{h}{(y_1 - y_2)} \quad (5)$$

Equations (4) and (5) may be applied to determine screen coordinates corresponding to camera coordinates of the subject's pupil.

Eye Coordinates

As shown in FIG. 6, the region of the eye, as shown in FIG. 5, that sees the current target 620 can be determined based on the relative positions of the previous target 610 (assuming that the subject's gaze is still directed to previous target 610 and the current target 620. FIG. 5 shows a grid representing the retina (eye coordinates). FIG. 6 shows a grid representing the primary display (screen coordinates).

Screen to Eye

Let the previous target 610 be the centre of the eye grid (FIG. 5). The relative distance from the previous target 610 to the current target 620 is the same on both grids, the retina grid in FIG. 5 and the screen grid in FIG. 6.

Eye to Screen

The relative distance from the centre of the eye grid is the same as the relative distance between the previous target 610 and the new target 620.

Pupil Movement Matching

Figure 7:
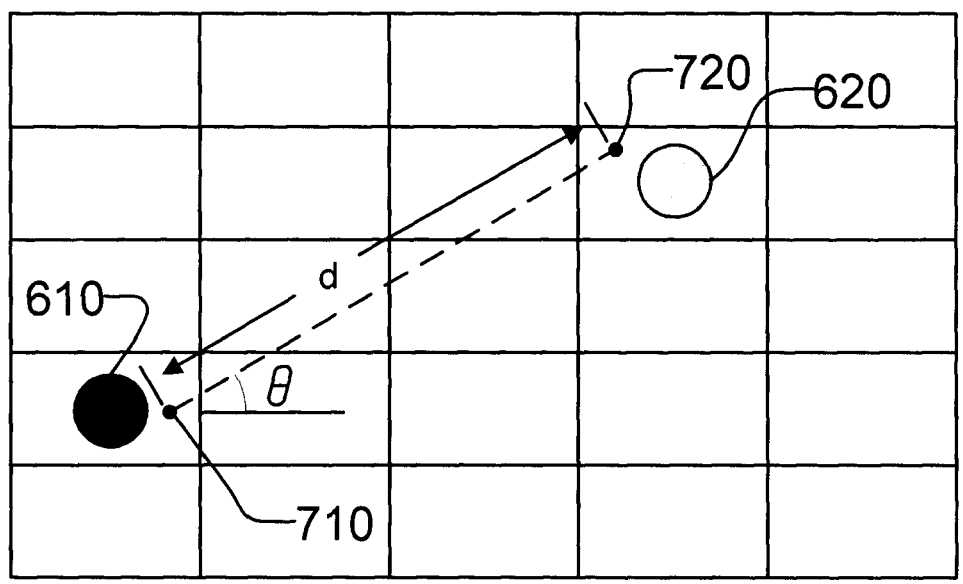
FIG. 7 illustrates the calculation of eye movement in response to new targets.

As illustrated in FIG. 7, motions of the subject's eye, as determined by gaze detection system 13 may be used to determine whether or not the subject has detected the current target 620 shown at a given position on primary display 200. This may be accomplished by comparing the eye's current position 720 relative to its position 710 when the previous target was shown to the relative distance between the current target 620 on primary display 200 and the previous target 610.

FIG. 7 illustrates how $\theta$ and d can be found for the relative positions of the two eye positions 710 and 720. $\theta$ and d can be found similarly for the relative position of the two targets 610, 620. These two sets of $\theta$'s and d's may then be compared to see if they agree within a reasonable margin of error. If they agree, then it is likely that the subject did detect the new target 620 at the corresponding eye grid position 720. If the subject's gaze does not shift toward the location of the new target within a reasonable time (e.g. 1 or 2 seconds or so) then the subject may be deemed to have failed to see the new target.

Target Generator

Apparatus 11 comprises a target generator that generates locations at which targets are displayed on screen 210 to test the subject's visual field. The target generator may comprise computer software instructions executing on computer 10 for example. A target generator begins by choosing a target location somewhere in the eye grid (FIG. 7) that has not yet been tested sufficiently. The target generator checks to see if the target location corresponds to a location on screen 210 (i.e. a location within the screen grid—FIG. 6). If not then the target generator selects another target location. In the alternative, the target generator generates target locations that always correspond to locations on the screen grid.

If no area of the subject's visual field that has not yet been tested sufficiently corresponds to a location on screen 210 then the target generator may select a location that has already been tested sufficiently but corresponds to a location on screen 210. For example, the target generator may set the location of the next target to be on a line between the previous target 610 and the target that was presented immediately prior to target 610. The next target may be at the midpoint of the line between the previous target 610 and the target that was presented immediately prior to target 610 for example.

A new target may be displayed at suitable intervals, for example every few seconds, for example every 1 or 2 seconds or so, until testing is complete. A new target may be displayed after the subject sees a previous target (as determined by the subject's gaze moving to the previous target) or the subject fails to see a previous target (as determined by the subject's gaze not shifting to the previous target within a threshold time period). The times between displaying successive targets may be varied somewhat, for example randomly.

Targets may be round. For example, targets may be circles displayed on screen 210 of primary display 200. This is not mandatory however. In some embodiments, targets may comprise other shapes or images such as small icons or pictures. Icons or pictures may motivate small children, for example, to try to see new targets as they are presented. The targets may have a suitable color that contrasts with a background presented on screen 210. For example, the targets may be white or red and the background may be black. This is not mandatory, however. In some embodiments, contrast between the targets and the background is adjustable either by an operator or automatically. Each displayed target may comprise a plurality of pixels of primary display 200 operated to have an appearance contrasting with a background on display 200.

Testing may continue until sufficient targets have been displayed to test sufficiently each region in the subject's visual field that it is desired to test. In some embodiments, the subject's visual field is divided into a number of regions and testing continues until at least two targets have been displayed at locations corresponding to each region of the visual field. Testing may be continued until results have been confirmed for each region. For example, in some embodiments if the subject either succeeds or fails to see both of two targets in a region then the region may be considered to have been tested sufficiently. If the subject succeeds on one test in a region and then fails on the second test in the region then the results may be considered inconclusive and additional targets may be displayed at locations corresponding to the region. To limit the time taken for a test, the number of times targets are displayed at locations in one region may be capped at a reasonable number. In some embodiments, each region is tested no more than three times, for example.

The visual field may be divided into any reasonable number of regions. The regions do not need to be equal in size although they may be. In some embodiments, the visual field is divided into nine to about 150 regions. For example, the visual field may be divided into an array of regions that is 3×3, 7×7, 12×12 or the like.

Medically relevant scotomas tend to affect fairly large areas of vision and thus, for many applications, it is not necessary to test at a very high resolution. For example significant diagnoses can be made based on dividing the visual field of a single eye into a 4 by 4 grid—that is, the field of vision is divided only into 16 parts. More significant data is obtained if the field of vision is more finely subdivided for example into a 5 by 5 grid (25 subdivisions), a 5 by 4 grid (20 subdivisions), a 5 by 6 grid (30 subdivisions) or even a 6 by 6 grid (36 subdivisions).

Scotomas (blind spots) from different levels of damage in the optic pathway often begin in different areas of the visual field. Glaucoma evolves first around the normal blind spot in the central field, which is where the optic nerve leaves the eye thus not a light receptive area. While brain damages along the optic nerve pathway tend to affect more temporal instead of central locations. The target generator may be configured to concentrate on some areas accordingly. In some embodiments, a user of apparatus 11 can specify particular regions of the visual field in which testing should be concentrated. The target generator may emphasize those regions or focus exclusively on those regions in some embodiments.

In some embodiments, a target on screen 210 is initially displayed as a single small point, then dynamically enlarged until a response occurs. For example, the target may be displayed first as a circle having a small diameter, such as 0.5 cm. The direction and speed of enlargement can be controlled.

When the initial target is within the confines of a real scotoma, the enlarging target will eventually cross the scotoma's boundary and elicit a response. Refining tests may be conducted to determine the exact intact areas of the subject's visual field.

Refining Test

In some embodiments, the test is refined. Refinements may be provided in various ways. For example, if a subject fails to see targets at a particular location on the eye grid, the target generator may test slight variations in location, still within the same region, to determine whether the subject can see targets at the varied locations. In one optional embodiment, if the subject fails to see targets at a location on the eye grid, additional targets slightly larger and/or brighter than the previous targets may be displayed at or near the location. This can be repeated, as necessary with larger and larger targets until the subject detects the target. It is not necessary to expand the target evenly. The computer program can be adjusted such that the target expands preferentially towards a region of the visual field where more data is desired.

In some embodiments, computer 10 is programmed to screen all or a selected portion of the subject's visual field by displaying targets at locations scattered around the part of the visual field being tested. Subsequently, expanding targets may be provided in areas in which the subject failed to see targets during the screening.

In some embodiments, apparatus 11 includes extension means for extending the visual field that can be tested using display 200. The means may comprise fixation lights 17 or other fixation targets (not shown) outside of display 200 or an additional display 201 capable of displaying targets or the like. The extension means may be controllable by computer 10.

Some pathologies, such as glaucoma, generally manifest themselves through deterioration of vision in the peripheral areas of the visual field. Many pathologies such as macular degeneration and many neurological condition manifest themselves with loss of vision in a more central portion of the field. To help diagnose these latter pathologies it may be necessary to test only the central portion of the visual field. It may only be necessary to test the central 15°, 20°, 25°, 30°, 40°, 50°, 60°, or 70° to help diagnose certain pathologies. While in other cases it is desirable to test the full visual field. Apparatus 11 may be configured to test only a selected portion of the visual field.

Figure 8:
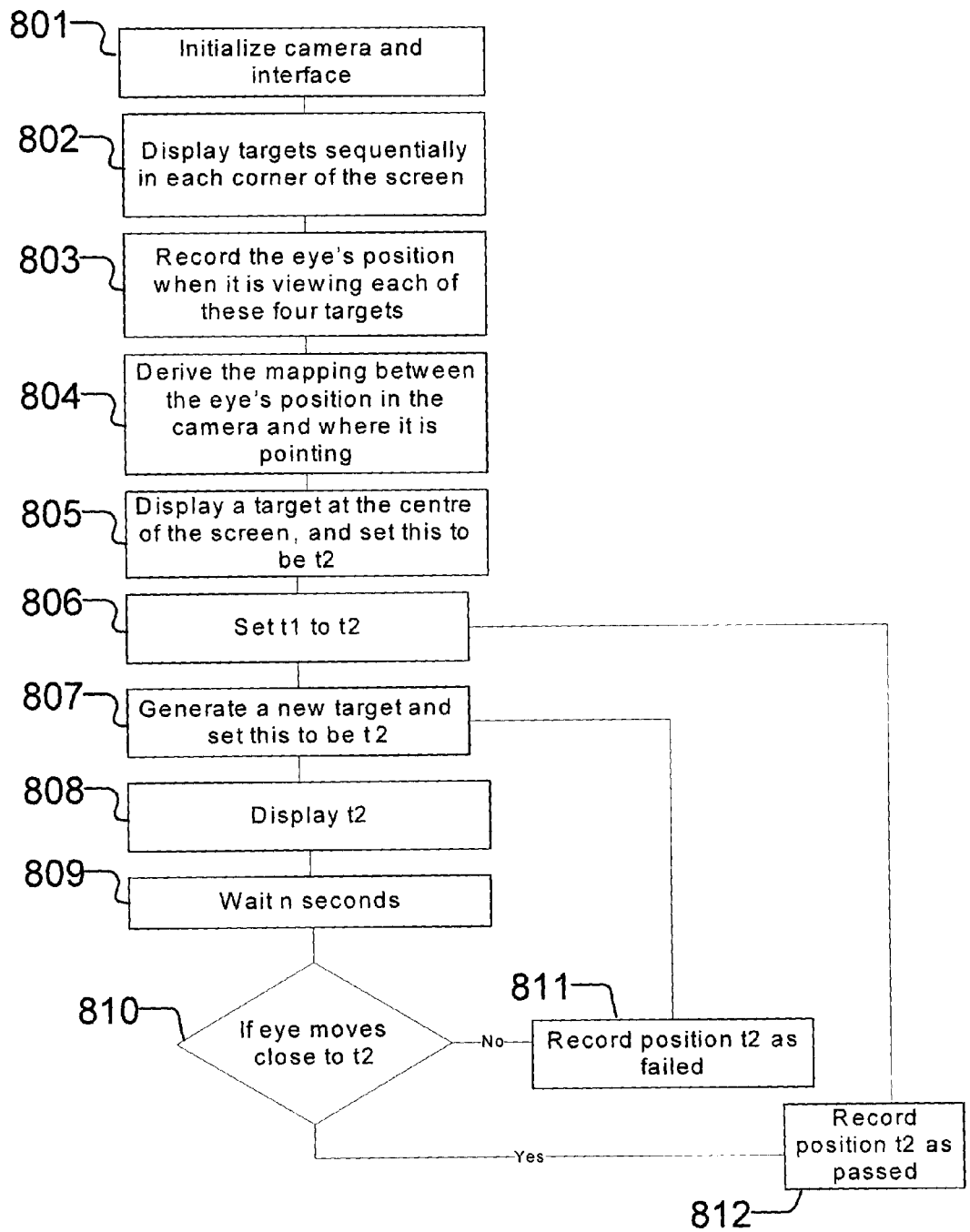
FIG. 8 is a flow chart of program logic in a method according to an example embodiment.

FIG. 8 is a flow chart illustrating an example method for testing the visual field of an eye. FIG. 8 illustrates both steps performed by software operating on the computer 10 as well as instructions given to a subject. In some embodiments, instructions may be given to the subject by displaying the instructions on primary display 200, presenting the instructions by way of a speech synthesizer, presenting prerecorded audio instructions or the like.

In step 801, apparatus 11 is initialized, and the hardware systems are set up. The subject is instructed to place his or her chin on the proper position (for example on chin rest 310). Vision of one eye is blocked by instructing the subject to close one eye or using physical means such as an eye patch, to cover the other eye—eyes are tested one at a time.

In step 802, targets are displayed sequentially at enough locations on screen 210 to permit calibration. The targets may be displayed in each corner of screen 210 for example. The subject is instructed to move his or her eye to look toward the target showing on the screen.

In step 803 the positions of the eye when looking at the targets displayed in step 802 are recorded. Where the targets are at the four corners of screen 210 the parameters $x_1$, $x_2$, $y_1$, $y_2$ for formulas (2) to (5) are obtained.

In step 804, the parameters $x_1$, $x_2$, $y_1$, $y_2$ obtained from step 803 are used to setup formulas (2)-(5).

Step 805 displays a target at a defined position, $(x'_{s2}, y'_{s2})$, which may be in the centre of screen 210 or at another location on screen 210, and sets this to be target t2. The subject is requested to look at the target t2, although there is a natural tendency for the eye to be drawn to a target so the request is not essential. The system then finds the eye position in camera 110, which will be used to find the corresponding position $(x_{s2}, y_{s2})$ on the display according to formulae (4) and (5); this is then compared with target t2 $(x'_{s2}, y'_{s2})$, and it is determined if the eye of the subject is directed towards target t2. This is repeated until it is determined that the eye of the subject is directed at target t2.

Step 806 sets t1 equal to t2, and accordingly sets $(x_{s1}, y_{s1})$ to $(x_{s2}, y_{s2})$ and sets $(x'_{s1}, y'_{s1})$ to $(x'_{s2}, y'_{s2})$. Now, the original t2 is the fixed target t1. With the eye of the subject directed to t1, it is determined if the eye reacts to a new target t2 presented somewhere on the screen, thus testing a position in the subject's visual field.

Step 807 generates a new target t2 $(x'_{s2}, y'_{s2})$ on screen 210 to test whether the subject will notice the target.

Step 808 displays the new target t2 on screen 210.

Step 809 waits for a predetermined length of time during which the eye is repeatedly tested (step 810) to determine if the eye has moved toward target t2. Note that step 809 overlaps with step 810.

Step 810 monitors the position of the eye $(x_c, y_c)$ as seen by camera 110 and calculates the position $(x_{s2}, y_{s2})$ at which the eye rests on display 210 according to formulae (4) and (5). The positions of t1 $(x'_{s1}, y'_{s1})$ and t2 $(x'_{s2}, y'_{s2})$ on screen 210 are known. The distance between $(x'_{s2}, y'_{s2})$ and $(x_{s2}, y_{s2})$ is calculated and it is determined whether the eye has become redirected to t2 within a predetermined margin of error.

At step 811, if after the predetermined time, there has not been movement of the eye toward t2, the system records this as a missed point—this point in the visual field is recorded as a potential blind spot.

At step 812, if the eye has moved to position t2 within the predetermined margin of error, it is assumed that the eye has detected the target at t2 and this point in the visual field is recorded as probably having functional vision.

Points within both potential blind spots and areas of probable vision within the visual field are preferably checked more than once to reduce random errors.

In embodiments as described herein, a computer 10 may display, store, or further process data representing results of a visual field test. For example, a computer 10 may create a map showing where the subject's eye is and is not sensitive, a table or other data structure indicating the success rates of each region in the subject's eye or the like.

The example embodiments described above reduce and generally eliminate the need for a subject to provide any verbal response or body/hand action to indicate that a target is, or is not, visible. The subject will only be required to follow the simple instruction: "When you see an object new appearing on the screen, look at the new object" and even this is not essential as it is natural for an eye to be drawn to a new object suddenly appearing in the field of view.

Some embodiments can be used for visual field testing of non-verbal subjects who may not have manual dexterity for pressing a button to show a response, as the change in gaze is already an indication when the subjects are instructed correctly not to change gaze unless a new target appears. Unlike the center-fixation designs, this reduces the boredom of subjects staring at one single target for the whole duration of a tedious, prolonged testing.

In addition to increasing the objectivity of visual field tests, various embodiments of this invention can also reduce the time needed to conduct visual field tests. Certain embodiments may also significantly reduce the cost of equipment to conduct visual field tests. Some embodiments are particularly suited to provide information for the diagnosis of neurological problems.

Although an embodiment described herein tests directly in front of the screen, there is no reason this must be so. The same hardware, algorithms and ideas could be applied to a variety of uses. For example, the range of normal vision extends nearly 200° horizontally in front of the eyes. By making the subject centre their vision on some point outside the display, and testing to see if the subject can see targets on the display, it is possible to test the entire field of vision, instead of the limited field described by the display.

As will be readily evident to one skilled in the art it is possible to use this apparatus with other standard, or non-standard, visual field tests; various modification are possible without departing from the inventive concept and it is possible to use the "expanding target" test with at least some other devices designed for measuring visual field.

In some embodiments, apparatus comprises a data processor that executes software instructions that cause it to perform visual field testing in the general manner as described herein. The software instructions may be stored in a memory accessible to the data processor. Aspects of the invention may be provided in the form of program products. The program products may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The computer-readable instructions on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for performing objective perimetry visual field testing of an eye of a subject, the method comprising:
   providing, in combination, an eye tracking device, a computer device and one or more display screens connected to display targets for viewing by the subject;
   displaying targets in sequence on one of the one or more display screens while the subject views the display screen with an eye under test; and
   recording whether the eye under test moves in response to the presentation of a target;
   wherein recording whether the eye under test moves in response to the presentation of the target comprises:
   with a camera, obtaining one or more first images of the eye under test while the eye under test is illuminated by a first illuminator;
   with the camera, obtaining one or more second images of the eye under test while the eye under test is illuminated by a second illuminator;
   processing pairs of the first and second images to determine positions of the pupil of the eye under test;
   determining a first angle and distance over which a point on the display at which the subject's eye is gazing moves and comparing the first angle and distance to a second angle and distance between a current target and an immediately-preceding target; and
   recording whether the position of pupil of the eye under test changes when a target is presented;
   wherein the first and second illuminators are arranged to generate contrasting images of the pupil of the eye under test.

2. A method according to claim 1, comprising testing only a central portion of the visual field of the subject's eye.

3. A method according to claim 2, wherein the central portion includes 15°, 20°, 25°, 30°, 40°, 50°, 60°, or 70° from the direction of gaze of the eye.

4. A method according to claim 1, the method comprising:
   creating an eye grid of an eye under test corresponding to a screen grid on at least one of the one or more display screens viewed by the subject;
   determining from the camera images a location on the eye grid and a corresponding location on the screen grid;
   determining from the locations whether the subject's eye has moved in response to presentation of a target;
   storing the location of each target and whether the subject's eye moved in response to the presentation of the target; and
   analyzing stored data to provide the perimetry visual field of the eye.

5. A method according to claim 1 wherein displaying targets includes starting each target as a single small point and then enlarging the target until an eye response occurs.

6. Apparatus for performing objective perimetry visual field testing of an eye of a subject, the apparatus comprising:
   an eye tracking device;
   a computer having one or more display screens;
   said computer comprising means for displaying targets in sequence on at least one of the one or more display screens while the subject views the display screen with an eye under test; and
   said computer having a memory and configured to determine from an output of the eye tracking device and record in the memory whether the eye under test moves in response to the presentation of a target
   wherein the eye tracking device comprises a camera and first and second illuminators the first and second illuminators arranged to generate contrasting images of the pupil of the eye under test and the computer is configured to process a first image of the eye under test while the eye under test is illuminated by the first illuminator and a second image of the eye under test while the eye under test is illuminated by the second illuminator to determine a position of the pupil of the eye under test wherein recording whether the eye under test moves in response to the presentation of the target comprises determining a first angle and distance over which a point on the display at which the subject's eye is gazing moves and comparing the first angle and distance to a second angle and distance between a current target and an immediately-preceding target.

7. Apparatus according to claim 6 wherein the computer comprises a personal computer.

8. Apparatus for performing objective perimetry visual field testing of an eye of a subject, the apparatus comprising:
a display device for viewing by said subject;
a gaze detection system for detecting and tracking the pupil of an eye under test, said system including an infrared camera and associated first and second infrared illuminators which emit radiation substantially invisible to the human eye but detectable by the camera;
the first illuminator being closer to the optical axis of the camera than the second illuminator;
means for detecting from images from said camera the location of a pupil of the eye under test;
a target generator for generating and displaying a sequence of targets on said display device;
a storage device for storing a location of each target and whether the eye moved in response thereto; and
means for processing stored target data to provide perimetry visual field of the eye
wherein storing whether the eye under test moves in response to the presentation of a target comprises determining a first angle and distance over which a point on the display at which the subject's eye is gazing moves and comparing the first angle and distance to a second angle and distance between a current target and an immediately-preceding target.

9. Apparatus according to claim 8 wherein said gaze detection system further includes means for alternately capturing even and odd frames of camera images in synchronism with activation of said first and second illuminators.

10. Apparatus according to claim 7 wherein said illuminators comprise infrared LEDs.

11. Apparatus according to claim 8 wherein said first illuminator comprises a ring of light emitting diodes (LEDs) around the lens aperture of the camera.

12. Apparatus according to claim 11, wherein LEDs in said ring generate a bright pupil image and LEDs of the second illuminator generate dark pupil images.

13. Apparatus according to claim 8 wherein said target generator is operable to select a target somewhere in an eye grid of the eye under test, determine whether the selected target is within a screen grid of the display device, and if so, use the selected target as a next target.

14. Apparatus for performing objective, perimetry visual field testing of an eye of a subject, the apparatus comprising:
a computational apparatus;
a display device, viewed by a subject during a test, connected to said computational apparatus for displaying targets within a screen grid on said display device;
an infrared camera connected to said computational apparatus and which, during use, is directed toward an eye under test for taking images of the subject eye and transmitting said images to said computational apparatus;
first and second illuminators disposed to illuminate the subject eye under test;
a computer program product embodied in a machine readable medium, said program product being operable to cause said computational apparatus to display a sequence of targets at different points of said display device; determine from said images the direction and point of gaze of the subject eye under test after each target has been displayed; and store the location of each target and movement or lack of movement of the subject eye under test in response to the presentation of the target
wherein storing whether the eye under test moves in response to the presentation of the target comprises determining a first angle and distance over which a point on the display at which the subject's eye is gazing moves and comparing the first angle and distance to a second angle and distance between a current target and an immediately-preceding target.

15. Apparatus according to claim 14 wherein the computer program product is operable to cause said computational apparatus to determine a perimetry of a field of vision of the eye under test.

16. Apparatus according to claim 14, wherein said illuminators include near infrared light sources and said camera being sensitive to a wavelength of said light sources.

17. Apparatus according to claim 16 wherein said illuminators comprise 16 IR light emitting diodes (LEDs) distributed in two concentric rings, with eight LEDs in each ring, the axis of the rings being coaxial with an optical axis of the camera, the diameter of an inner one of the concentric rings being approximately the same as the diameter of a lens of the camera, and the diameter of an outer one of the concentric rings being larger than the diameter of the inner concentric ring.

18. Apparatus according to claim 16, wherein said illuminators comprise 16 IR light emitting diodes (LEDs) distributed in a ring and a pair of parallel lines, with eight LEDs in the ring and eight LEDs in the parallel lines, an axis of the ring being coaxial with an optical axis of the camera and the diameter of the ring being approximately the same as the diameter of a lens of the camera, and the parallel lines being spaced outwardly of the ring.

19. Apparatus according to claim 14 wherein said display device has a substantially flat screen.

20. Apparatus according to claim 14 wherein said computational apparatus comprises a personal computer.

21. Apparatus according to claim 6, wherein the camera is an infrared camera and the apparatus further comprising a machine-readable medium having instructions stored thereon capable of causing a processor of the computer to carry out steps comprising:
a) initializing the infrared camera and an interface between the camera and the computer;
b) defining an eye grid by sequentially displaying a target at each corner of at least one of the one or more display screens;
c) recording the position of the pupil of the eye under test when it is viewing each of the four targets;
d) deriving a mapping between the position of the eye in the camera and the direction in which the eye is pointing;
e) displaying a target at the centre of at least one of the one or more display screens and assigning the location of the target to target t2;
f) setting the location of a target t1 equal to the location of target t2;
g) generating a new target within said grid and assigning its location to target t2;
h) displaying target t2 on said at least one of the one or more display screens for a predetermined period of time;
i) determining whether the eye has moved close to the location of target t2 and, if not, recording target t2 as failed and then repeating steps (g) onward; and if so, recording target t2 as passed and repeating steps (f) onward until a target t2 is found that has failed; and, j) processing the recorded data to provide the result of an objective perimetry visual field of the eye under test after displaying a predetermined number of targets.

22. A method according to claim 1 wherein displaying targets includes starting each target at an initial brightness and then increasing the brightness until an eye response occurs.

23. A method according to claim 5, the method further comprising:
a) initializing the camera and an interface between the camera and the computer device;
b) defining an eye grid by sequentially displaying a target at each corner of at least one of the one or more display screens;
c) recording the position of the pupil of the eye under test when it is viewing each of the four targets;
d) deriving a mapping between the position of the eye in the camera and the direction in which the eye is pointing;
e) displaying a target at the centre of at least one of the one or more display screens and assigning the location of the target to target t2;
f) setting the location of a target t1 equal to the location of target t2;
g) generating a new target within said grid and assigning its location to target t2;
h) displaying target t2 on said at least one of the one or more display screens for a predetermined period of time;
i) determining whether the eye has moved close to the location of target t2 and, if not, recording target t2 as failed and then repeating steps (g) onward; and if so, recording target t2 as passed and repeating steps (f) onward until a target t2 is found that has failed; and,
j) processing the recorded data to provide the result of an objective perimetry visual field of the eye under test after displaying a predetermined number of targets.

\* \* \* \* \*